United States Patent
Yu et al.

[11] Patent Number: 6,056,729
[45] Date of Patent: May 2, 2000

[54] ORNAMENTAL ARTICLE FOR TRANSDERMAL DRUG DELIVERY

[76] Inventors: Min-Tseng Yu, No. 11, Alley 14, Lane 25, Ching-Lung St., Ta-Liao Hsiang, Kaohsiung Hsien; Yung-Sheng Lin, No. 364, Fu-Hsing Rd., Lu-Kang Chen, Chang-Hua Hsien, both of Taiwan

[21] Appl. No.: 09/169,201

[22] Filed: Oct. 9, 1998

[51] Int. Cl.[7] .................................................. A61M 35/00
[52] U.S. Cl. .................................................. 604/289; 63/3
[58] Field of Search .................................. 604/289, 290, 604/23; D11/3; 63/1.1, 1.14, 3, 23; 206/530, 531, 532, 534

[56] References Cited

U.S. PATENT DOCUMENTS

| | | |
|---|---|---|
| 2,510,224 | 6/1950 | Hettinger . |
| 4,078,660 | 3/1978 | Lerro ........................ 206/530 |
| 4,624,656 | 11/1986 | Clark et al. ................. 604/289 |
| 4,781,705 | 11/1988 | Shepherd et al. ............ 604/289 |
| 4,801,291 | 1/1989 | Loori ........................ 604/289 |
| 5,007,252 | 4/1991 | Mochizuki ..................... 63/3 |
| 5,030,214 | 7/1991 | Spector ..................... 604/301 |
| 5,259,835 | 11/1993 | Clark et al. ................. 604/48 |
| 5,528,909 | 6/1996 | Tonakawa ..................... 63/3 |

*Primary Examiner*—Ronald Stright
*Assistant Examiner*—David J. Cho
*Attorney, Agent, or Firm*—Christie, Parker & Hale, LLP

[57] ABSTRACT

An ornamental article for transdermal delivery includes a ring-shaped member adapted to be put around a body to be treated. The ring-shaped member has at least one drug storing cavity formed therein, and at least one drug delivery channel communicated with the drug storing cavity and extending to an inner periphery of the ring-shaped member. A drug stored in the drug storing cavity can be released via the drug delivery channel to the skin of the body when the ring-shaped member is moved upon movement of the body.

6 Claims, 4 Drawing Sheets

ORNAMENTAL ARTICLE FOR TRANSDERMAL DRUG DELIVERY

BACKGROUND OF THE INVENTION

1. Field of the Invention

This invention relates to an ornamental article for transdermal drug delivery for medical treatment or health care, more particularly to an article which is used for transdermal drug delivery for medical treatment or health care and which possesses an aesthetic appearance so as to be suitable for use as a body ornament.

2. Description of the Related Art

Various routes of drug delivery, such as skin contacting drug delivery patches or pads, oral drug delivery and drug injection delivery, have been available in the art for medical treatment. Each has its own advantages and disadvantages. Skin contacting drug delivery patches or pads involve direct attachment to the skin of the wearer such that the drug can be absorbed through the skin into the human body to effect the therapy. The drug coated on the pad is usually made wet and sticky which, when applied, often causes the wearer to feel uncomfortable and irritated. These symptoms are more apparent when the pad is applied for a long period of time. As such, skin contacting drug delivery patches or pads are generally used only when treating injuries, such as broken skin, swelling muscle, injured tendons, or the like, that need a short time period in the course of medical treatment. In addition, the structure and appearance of conventional skin contacting drug delivery patches or pads are not aesthetic. Therefore, it is unlikely that a person would use it for the purpose of disease prevention or health care, especially under long periods of time.

Oral drug delivery requires a patient to swallow the drug, which normally is in tablet, capsule, or powdered form, in order to deliver the drug to the digestive system so that the drug can be absorbed by the human body. It is known that most oral drugs can have a deleterious effect to the digestive system. Particularly, oral drugs may upset the digestive system or may cause serious problems that can hinder the proper functioning of the digestive system, especially after a long time of use. Moreover, oral drugs, if used inappropriately or carelessly, which happen quite often, can poison the user.

Drug injection requires the puncturing of a sharp item into the human body and is frequently used as an effective route for drug delivery into the human body. However, this route is quite uncomfortable and painful for the patient. When there is direct injection of the drug into the circulating system of the human body, the loading of the circulating system is raised, and the accompanying deleterious effect is also increased. No misuse can be allowed. Therefore, a person is often unwillingly to opt for the drug injection delivery for medical treatment unless absolutely necessary.

In addition, these drug delivery routes, which need to be used cautiously under prescribed dosages and indicated times may sometimes be easily neglected or misused, thus leading to an adverse affect to the medical treatment. The aforesaid drug delivery routes are therefore not suitable for a long course of medical treatment or health care.

As described above, while the aforesaid routes are commonly used in medical treatment, a common disadvantage of these routes exists, i.e., they are not suitable for medical treatment of chronic disease, or for disease prevention, or for health care that would require a long course of medical treatment.

There is therefore a need to provide a drug delivery device that is suitable for a long course of use without resulting in any of the above-described disadvantages.

SUMMARY OF THE INVENTION

The object of this invention is to provide an ornamental article that can be worn by a patient and that can contain a drug capable of transdermal delivery.

According to one aspect of the invention, an ornamental article for transdermal drug delivery comprises a ring-shaped member adapted to be put around a body to be treated. The ring-shaped member has an inner periphery adapted to contact the skin of the body, at least one drug storing cavity formed inside the ring-shaped member, and at least one drug delivery channel communicated with the drug storing cavity and extending to the inner periphery. A drug stored in the drug storing cavity can be released via the drug delivery channel to the skin of the body when the ring-shaped member is moved upon movement of the body.

In another aspect of this invention, an ornamental article for transdermal drug delivery comprises a ring-shaped member adapted to be put around a skin of a body to be treated. The ring-shaped member has a plurality of bead elements and a string to thread through the bead elements. Each of the bead elements has a string hole and an inner periphery confining the string hole. At least one of the bead elements has a drug storing cavity radially spaced apart from the string hole thereof, and a drug delivery channel communicated with the drug storing cavity and extending to the inner periphery. A drug stored in the drug storing cavity can be released via the drug delivery channel to the string and then to the skin of the body when the ring-shaped member is moved upon movement of the body.

The object and advantages of this invention will be readily apparent from the following description with reference to the accompanying drawings.

DESCRIPTION OF THE PREFERRED EMBODIMENTS

Figure 1:
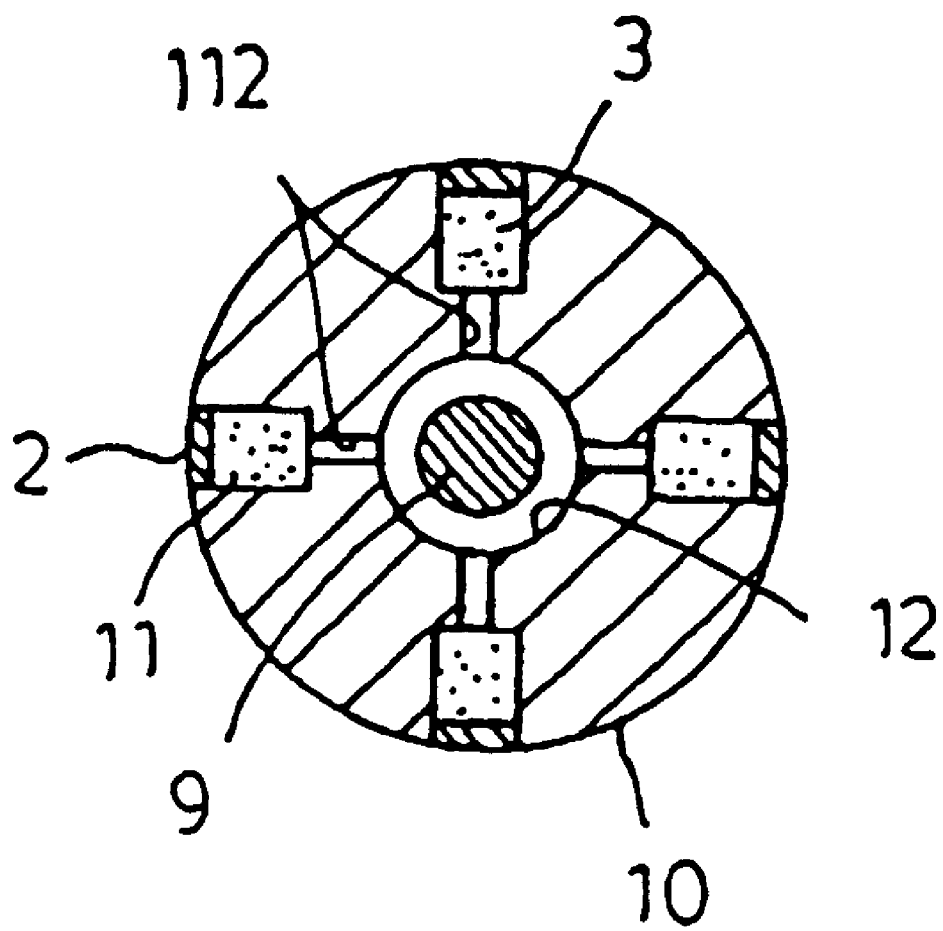
FIG. 1 is a sectional view of the a bead element used in a preferred embodiment of an ornamental article of this invention.

As illustrated in FIG. 1, four drug storing cavities 11 are formed in a bead element 10 to store a drug 3 and are annularly spaced apart from each other. One end of each of the drug storing cavities 11 is connected to a drug delivery channel 112, while the other end thereof extends to the outer surface of the bead element 10. Each drug delivery channel 112 is constricted so that it has a cross-section smaller than that of the corresponding one of the drug storing cavities 11. A string hole 12 is formed substantially in the center portion of the bead element 10 for passage of a string 9. The drug storing cavities 11 are radially spaced apart from and are communicated with the string hole 12 via the drug delivery channels 112. Each drug delivery channel 112 opens at the inner periphery of the bead element 10, which confines the string hole 12. A shield 2 is provided to close one end of each drug storing cavity 11 that extends to the outer surface of the bead element 10.

Figure 2:
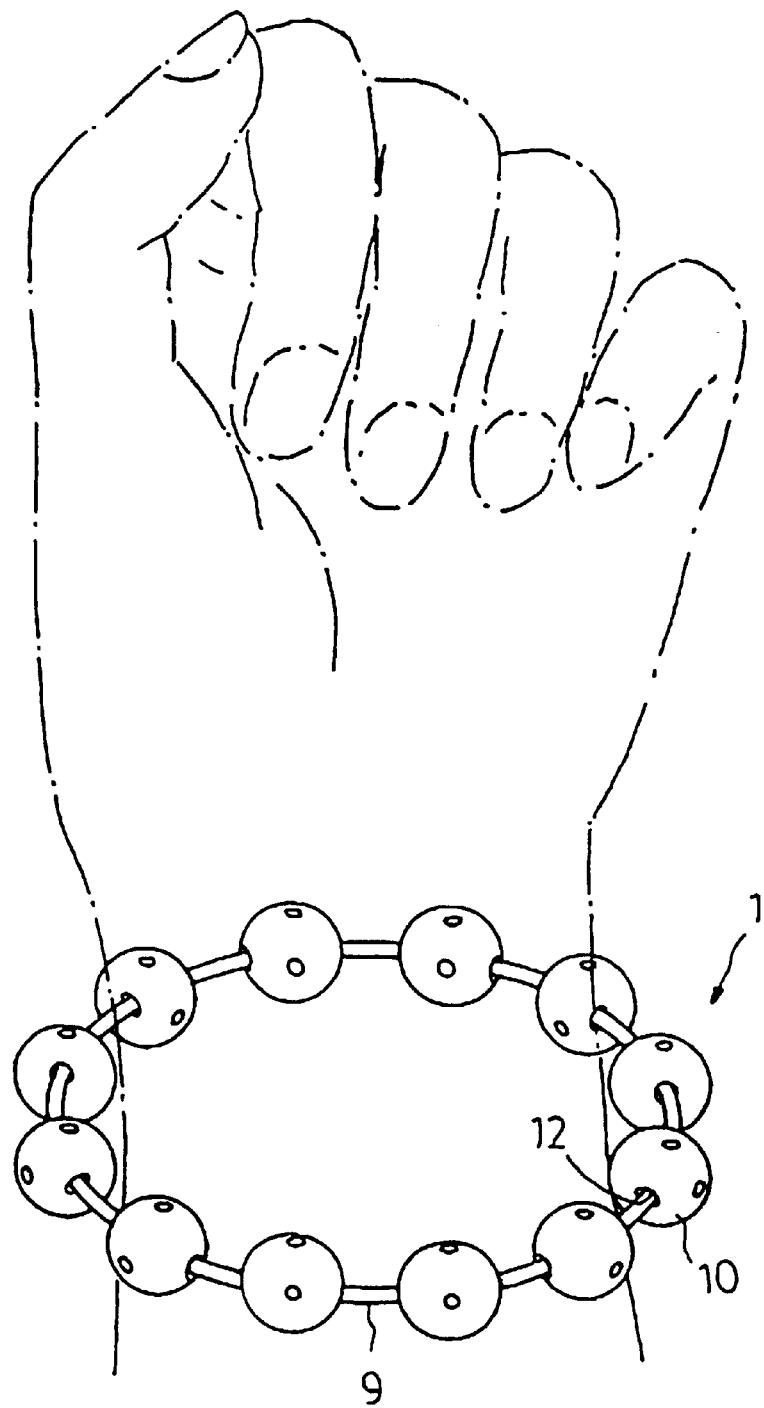
FIG. 2 is a perspective view of the preferred embodiment which comprises a plurality of the bead elements of FIG. 1.

FIG. 2 illustrates a preferred embodiment of an ornamental article of this invention which comprises a ring-shaped member configured as a bracelet 1. The bracelet 1 includes a plurality of the bead elements 10 assembled together via the string 9 shown in FIG. 1. The string 9 passes through each bead element 10 to form bracelet 1.

When bracelet 1 is put around the hand of a wearer, bead elements 10 are in contact with the hand. By shaking the hand or by sliding the bracelet 1 along the hand, the bead elements 10 can be moved, and the drug 3 can be released to the string 9 from the drug storing cavities 11 of the bead elements 10 through the drug delivery channels 112. The drug on the string 9 then falls onto and contacts the skin of the hand. Since the drug 3 implanted into the drug storing cavities 11 is of the type capable of transdermal delivery, the drug 3 will be delivered into the body of the wearer through the skin. Preferably, the drug 3 is in the form of a powder which can be moistened on the skin with the aid of the heat produced by the body of the wearer. The moistened drug 3 can thus be absorbed by the body of the wearer through the skin. Long contact between the skin and the bracelet can provide the effect of medical treatment of disease prevention.

Because of the constricted cross-sectional of the drug delivery channels 112, the releasing rate of the drug 3 can be controlled in a manner suitable for long term treatment.

Figure 3:
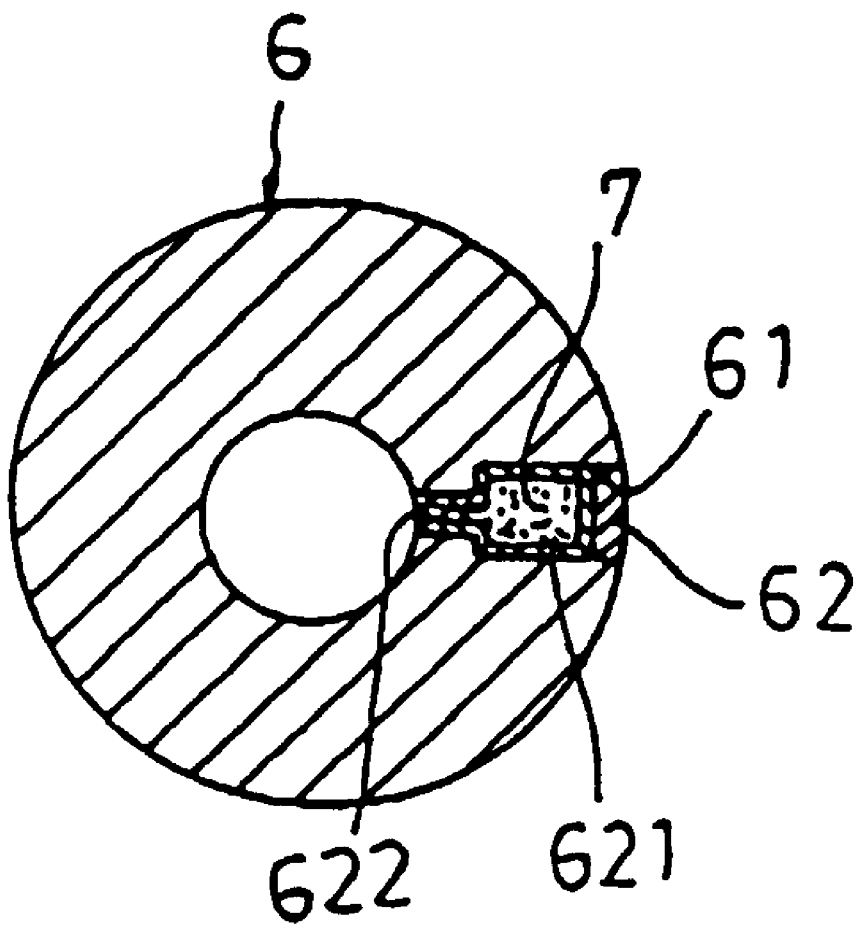
FIG. 3 is a sectional view showing another form of the bead element suitable for use in the embodiment of FIG. 2.

FIG. 3 shows another form of bead element 6 which can be used in the embodiment of FIG. 2 in place of the bead element 10. The bead element 6 is substantially the same as the bead element 10 except that a single drug storing cavity 61 is provided to store a drug 7. The drug storing cavity 61 is closed by a shield 62 at the outer periphery of the bead element 6. For the sake of convenience in manufacture or in use, the drug 7 is encapsulated in a bag 621 which is pervious to the drug 7. In assembly, the bag 621 filled with the drug 7 is first put into the drug storing cavity 61. Thereafter, the bag 621 is cut to remove its sealed end, and the resulting cut end is directed to and is communicated with a drug delivery channel 622. As such, the drug 7 can be released out at a relatively slow rate. When the drug 7 is used up, the empty bag 621 can be replaced with another bag filled with the drug.

Figure 4:
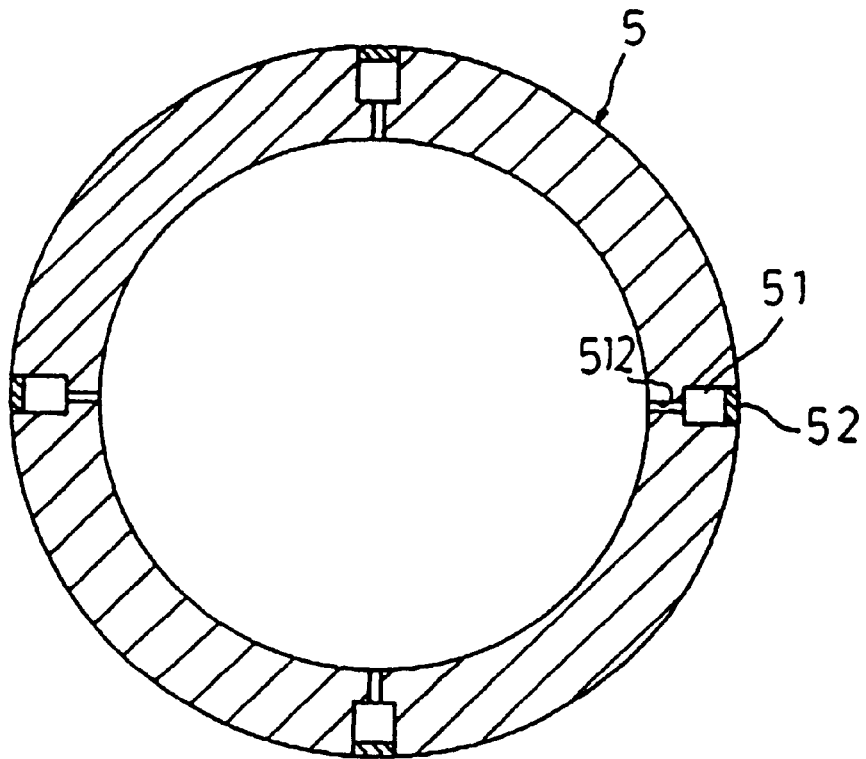
FIG. 4 is a cross-sectional view of another preferred embodiment of an ornamental article of this invention.
Figure 5:
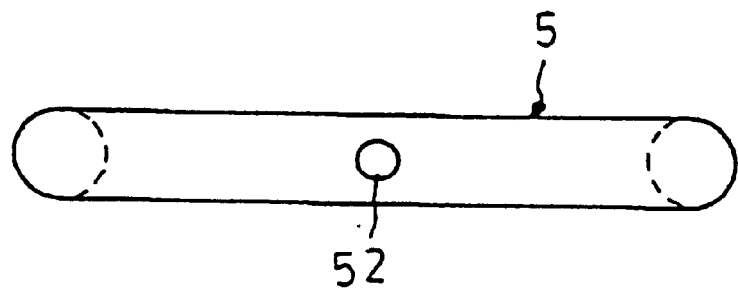
FIG. 5 is a side view of the ring-shaped member of FIG. 4.

FIG. 4 and FIG. 5 illustrate another preferred embodiment of an ornamental article of this invention, which has a one-piece ring-shaped member configured as a bracelet 5. Like the bead element 10, the bracelet 5 also comprises four drug storing cavities 51 closed by respective shields 52 at an outer periphery of the bracelet 5, and four drug delivery channels 512 respectively communicated with the drug storing cavities 51 and extending to an inner periphery of the bracelet 5. The inner periphery of the bracelet 5 can directly contact the skin of the wearer. Hence, without the string 9 as a medium for transferring the drug to the skin of the body as described in the embodiment of FIG. 2, the drug stored inside the drug storing cavities 51 can be directly delivered through the drug delivery channels 512 to the skin upon movement of the bracelet 5 on the hand of the wearer.

With this invention thus explained, it is apparent that numerous modifications and variations can be made without departing from the scope and spirit of this invention. It is therefore intended that this invention be limited only as indicated in the appended claims.

We claim:

1. An ornamental article for transdermal drug delivery, comprising:

a ring-shaped member adapted to be put around a body to be treated, said right-shaped member having:
    an inner periphery adapted to contact the skin of the body,
    a plurality of drug storing cavities formed inside said ring-shaped member, and
    a plurality of delivery channels communicated with the plurality of drug storing cavities and extending to said inner periphery, such that a drug stored in the plurality of drug storing cavities can be released via one of the plurality of drug delivery channels to the skin of the body when said ring-shaped member is moved upon movement of the body;
wherein said ring-shaped member is configured as a bracelet and the plurality of drug storing cavities being annularly spaced apart from one another, each of the plurality of drug delivery channels having a constricted cross-section smaller than that of the corresponding one of the plurality of drug storing cavities, such that the drug stored in one of the plurality of drug storing cavities can be released via a corresponding one of the plurality of drug delivery channels to the skin of the body in a relatively slow rate that is suitable for a long course of medical treatment.

2. The ornamental article of claim 1 wherein the drug stored in one of the plurality of drug storing cavities is a transdermic drug.

3. The ornamental article of claim 1 wherein the plurality of drug storing cavities are opened at an outer periphery of said ring-shaped member, said ring-shaped member further having a plurality of shields at said outer periphery to close each of the plurality of drug storing cavities.

4. An ornamental article for transdermal drug delivery comprising:

a ring-shaped member adapted to be put around a body to be treated, said ring-shaped member having a plurality of bead elements and a string to thread through said bead elements, each of said bead elements having a string hole and an inner periphery confining said string hole, each of said bead elements having a drug storing cavity radially spaced apart from said string hole thereof, and a drug delivery channel communicated with said drug storing cavity and extending to said inner periphery, such that a drug stored in said drug storing cavity can be released via said drug delivery channel to said string and then to the skin of the body when said ring-shaped member is moved upon movement of the body;
wherein said ring-shaped member is configured as a bracelet and said drug delivery channel having a constricted cross-section smaller than that of said drug storing cavity, such that the drug stored in said drug storing cavity can be released via said drug delivery channel to the skin of the body in a relatively slow rate that is suitable for a long course of medical treatment.

5. The ornamental article of claim 4 wherein the drug stored in said drug storing cavity is a transdermic drug.

6. The ornamental article of claim 4 wherein each of said bead elements further has at an outer periphery provided with a shield to close said drug storing cavity.

* * * * *